United States Patent [19]

Dodge, III et al.

[11] 4,309,187

[45] Jan. 5, 1982

[54] METASTABLE ENERGY TRANSFER FOR ANALYTICAL LUMINESCENCE

[75] Inventors: William B. Dodge, III, Waynesboro; Ralph O. Allen, Charlottesville, both of Va.

[73] Assignee: University of Virginia Alumni Patents Foundation, Charlottesville, Va.

[21] Appl. No.: 88,122

[22] Filed: Oct. 25, 1979

[51] Int. Cl.³ ............................................. G01N 21/60
[52] U.S. Cl. .............................. 23/232 E; 315/111.01; 315/111.11; 356/316; 422/98
[58] Field of Search ......................... 23/232 E; 422/48; 313/201, 201.3, 201.4, 248, 234; 315/111, 111.1; 356/316

[56] References Cited

U.S. PATENT DOCUMENTS 2,068,741  1/1937  Geffcken et al. ................... 313/201
4,148,612  4/1979  Taylor et al. ..................... 23/232 E
4,150,951  4/1979  Capelle et al. .................... 23/232 E

OTHER PUBLICATIONS

Wulf et al., Physical Review, vol. 55, pp. 687–691, (1939).
Noxon, Journal of Chemical Physcis, v. 36, No. 4, pp. 926–940 (1962).

Primary Examiner—Michael S. Marcus
Attorney, Agent, or Firm—Oblon, Fisher, Spivak, McClelland & Maier

[57] ABSTRACT

A method and apparatus for analysis of atomic species which comprises directly forming metastable energy level nitrogen by processing a stream of nitrogen containing gas through a dielectric field wherein essentially no excited species above the 6th vibrational level of the $B^3\pi_g$ energy state nor nitrogen atoms nor ions are formed, admixing said excited nitrogen with a gas stream suspected of containing said atomic species to be analyzed whereby the energy level of said species is raised sufficiently to enable a fluorescent emission as the energy level of said excited species decays to its lower energy state, detecting and analyzing the spectrum of said flluroescent radiation to determine the identity and concentration of said element.

20 Claims, 3 Drawing Figures

MERCURY: EXCITATION IN DIELECTRIC DISCHARGE
AFTERGLOW     p = 1 torr
HgCl₂ ATOMIZED   5μl ALIQUOT   253.7nm LINE

METASTABLE ENERGY TRANSFER FOR ANALYTICAL LUMINESCENCE

BACKGROUND OF THE INVENTION

1. Field of the Invention

This invention relates to methods of analyzing atomic species by means of their emission spectra and more particularly to analysis of atomic species by emission spectra wherein the atomic species are excited to emit light by means of excited metastable gas molecules. Still more particularly, it relates to analysis of atomic species by means of their emission spectra wherein atoms of the atomic species are excited by contact with excited metastable nitrogen gas molecules.

2. Description of the Prior Art

Qualitative and quantitative analysis of atomic species in the vapor phase by means of their absorption or emission spectra are well known analytical chemical techniques. In atomic absorption spectroscopy, a beam of light is passed through a vapor containing the atomic species to be analyzed and the amount of the species present is determined by the amount of light absorbed by the vapor. In emission spectroscopy, the atomic species in the vapor phase are excited to emit fluorescent radiation and the spectrum and intensity of the emitted light are analyzed to determine which species are present and the concentration of each. Various methods of exciting atomic species to emit fluorescent radiation have been used, such as arcs, sparks, and flames. It is also known to excite the atomic species by contact with metastable atoms of an excited, relatively inert gas in a flowing gaseous medium.

Capelle, U.S. Pat. No. 4,150,951, discloses a method of analyzing for trace amounts of metals and other fluorescing species in the gas phase by introducing the species to be analyzed into a gas stream containing an energetic metastable species of nitrogen or a noble gas. The species to be analyzed is excited by contact with the metastable exciting species and subsequently emits fluorescence at characteristic wavelengths. The metastable species are produced by subjecting a gas stream containing a noble gas or nitrogen at pressures of less than 10 Torr to a microwave discharge. The method of Capelle is disclosed to be not useful at relatively high concentrations of metal atoms (about $10^{13}$ atoms/cm$^3$) because the amount of activating metastable species which can be produced by the microwave discharge will not adequately excite concentrations of metal atoms above this limit.

Taylor, U.S. Pat. No. 4,148,612, discloses a method of detecting and measuring trace impurities in a flowing gas system by mixing the gas with a second gas stream containing excited metastable species which transfer their energy to the trace impurities whereby the impurities themselves become excited and emit radiation. This emitted radiation is detected and analyzed by a conventional emission spectrometer, and the concentration of impurities may be determined in the usual way from the location and intensity of the lines in the emission spectrum. The method is disclosed as useful in analyzing any species which is capable of being excited by energy transfer from a metastable species and subsequently emitting the energy so acquired in the form of light in a spectral region where it may be detected.

Ault, U.S. Pat. No. 3,545,863, discloses a method for detecting trace amounts of mercury by excitation of the mercury vapor in a helium glow arc sustained by a glow discharge.

The known methods for analyzing atomic species in the gas phase, however, have suffered from a number of drawbacks.

Atomic absorption spectroscopy is capable of analyzing only a single element at a time, the apparatus required to vaporize the sample species is a rather complex apparatus, and a separate light source is required for the absorption measurement which requires a special lamp for each element to be analyzed.

The technique of choice used in the above Taylor and Capelle patents for generating the active metastable species is microwave discharge. Microwave discharge, in addition to requiring a relatively large, complex, and expensive apparatus, is a rather inefficient method of generating excited metastable species, particularly of nitrogen. This means that large amounts of power are dissipated, with attendant cooling requirements, and, most important, the actual concentrations of active species attained are rather small. This has the consequence that the available amount of metastable species is sufficient to excite only relatively small amounts of the sample species and, accordingly, only relatively small concentrations of the sample species can be accurately analyzed. The problems associated with this limited linear dynamic range are discussed by Capelle. Another difficulty with microwave discharges and other methods of generating excited metastable species which use a relatively large input of energy is that they produce, besides the desired metastable species, other luminescent species which contribute to the general background radiation observed by the detector ("noise") and may interfere with the emission from the desired sample species. This excess background radiation may limit the lowest concentration of sample species which can be accurately analyzed.

Microwave discharge, for instance, necessarily involves the generation of atomic nitrogen. Atomic nitrogen is a quencher for the metastable species such that when the metastable species comes into contact with atomic nitrogen, it spontaneously decays to the ground state. Thus, microwave generation is a poor source of metastable nitrogen. Moreover, while some of the nitrogen atoms will come together to form metastable nitrogen, much more of the nitrogen atoms will yield interfering higher excited species and will also react with oxygen atoms thereby considerably enhancing the spectral interference.

Hence, a need has continued to exist for a method of trace element analysis which has a high sensitivity and a large linear dynamic range, which is capable of analyzing more than a single element at a time, and which uses relatively simple and convenient apparatus.

SUMMARY OF THE INVENTION

Accordingly, it is an object of this invention to provide a method of analyzing for trace amounts of metals and other species capable of fluorescence by using metastable excited nitrogen molecules produced by a dielectric discharge to excite the fluorescence of the species to be analyzed.

A further object is to provide a method of analyzing for trace metals and other atomic species which has a high sensitivity.

A further object is to provide a method of analyzing for trace metals and other atomic species which has a large linear dynamic range.

A further object is to provide a method of analyzing for trace amounts of metals and other atomic species which is capable of analyzing relatively large concentrations of these species.

Another object of this invention is to provide an apparatus which can function at or near atmospheric pressure which will permit direct atmospheric sampling without substantial generation of interfering, specturally obscuring species.

It is a further object to provide a method of analyzing for trace amounts of metals which provides great sensitivity by reason of low background emission of the exciting metastable species.

It is a further object to provide a method of analyzing for trace amounts of metals which is capable of analyzing for more than one species at a time.

It is a further object to provide a method of analyzing for trace amounts of metals by excitation with active nitrogen which is not subject to interference from quenching species in the sample.

It is a further object to provide an improved apparatus for analyzing trace amounts of atomic species in the gas phase which is simpler and more convenient than known apparatus and is easier and more economical to operate.

These and other objects of this invention as hereinafter will become more readily apparent have been attained by providing a method for analysis for atomic species which comprises directly forming metastable energy level nitrogen by passing a stream of nitrogen containing gas through a dielectric field wherein essentially no excited species above the 6th vibrational level of the $B^3\pi_g$ energy state, nitrogen atoms, or ions are formed, admixing said excited nitrogen with a gas stream suspected of containing said atomic species to be analyzed whereby the energy level of said species is raised sufficiently to enable a fluorescent emission as the energy level of said excited species decays to its lower energy state, detecting and analyzing the spectrum of said fluorescent radiation to determine the identity and concentration of said element.

Apparatus for carrying out the claimed method is also provided wherein in an apparatus for analysis of atomic species which comprises excitation means for exciting nitrogen in a nitrogen-containing gas to a higher energy state, means for introducing a stream of nitrogen-containing gas into and through said excitation means, means for admixing said gas passing through the dielectric field with a gas stream suspected of containing the atomic species to be analyzed, so as to transfer the energy from said excited nitrogen to said atomic species whereby said atomic species if present is caused to flueoesce, and detection means for detecting said fluorescent radiation, the improvement comprises exciting said nitrogen in said nitrogen-containing gas in a dielectric field so as to produce essentially no excited species above the sixth vibrational level of the $B^3\pi_g$ energy state.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein.

DETAILED DESCRIPTION OF THE INVENTION AND PREFERRED EMBODIMENTS

Figure 1:
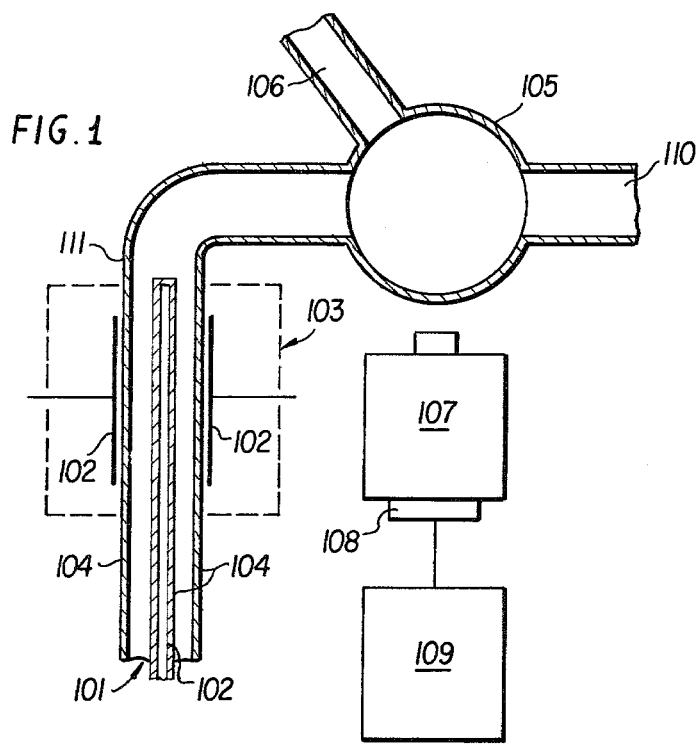
FIG. 1 is a schematic representation of an apparatus for performing the process of this invention.

The improved analytical method of this invention may be carried out by means of an apparatus such as that shown schematically in FIG. 1. Nitrogen gas is supplied from a source to conduit 101 which conducts the gas between the electrodes 102 of a dielectric discharge device 103. The walls 104 of the conduit or flow channel are made of a dielectric material, such as glass. The electrodes 102 are connected to a source of electric current having a voltage high enough to produce a dielectric discharge in the nitrogen passing through the dielectric discharge device 103. The stream of gas containing active nitrogen then proceeds through bend 111 to a reaction chamber 105 wherein it is contacted with the species to be analyzed. The bend 111 in the path acts as a light trap to further reduce background interference. The species to be analyzed may be originally in the solid, liquid or gaseous state. When it is in the gaseous state it need merely be introduced into the gas stream containing active nitrogen by means of a nozzle 106 as shown in FIG. 1. The gaseous sample may be introduced by itself or it may be mixed with a second carrier gas stream and introduced through the nozzle 106. If the sample is originally in the solid or liquid state it must be atomized by some conventional procedure in order to be mixed with the gas stream containing active nitrogen. This may be done by heating the sample to vaporize the sample or spraying a solution thereof either into the mixing chamber itself or into a second carrier gas stream which is introduced through nozzle 106. It is also possible to introduce a metal species to be analyzed in the form of a volatile compound which will be decomposed by the action of the active nitrogen to yield metal atoms in the vapor phase. In the reaction chamber the atomized species to be analyzed comes into contact with the excited metastable active nitrogen molecules. The excitation energy of the metastable nitrogen molecules is transferred to the atoms of the sample whereby they are raised to an excited electronic state. The excited atoms of the sample species then return to their ground states with emission of light in a fluorescence process. The light is emitted at characteristic wavelengths whereby a line spectrum is produced which is characteristic of the atomic species, as is well known. The intensity of the emission is proportional to the number of atoms of the species to be analyzed which are present in the reaction chamber. The reaction chamber is provided with a transparent wall or window through which the emission can be observed.

The spectrum is ordinarily analyzed by means of a monochromator 107 equipped with a conventional photoelectric detector 108 and recorder or storage device 109 to record the wavelength and intensity of the emitted fluorescent radiation.

More than one atomic species can be analyzed in the same sample by the simple expedient of providing multiple detectors or by employing a monochromator which scans the spectrum. After passing through the reaction chamber, the sample species and used nitrogen gas pass out of the reaction chamber through exit conduit 110. The flow of gas through the apparatus can be maintained for instance by a pressure differential between the source of nitrogen and the exit conduit. This pressure differential is maintained by using a pressurized gas source and/or a pump (not shown) at the exit conduit.

According to the present technique, nitrogen is excited by passing the source gas through a dielectric field. This results in "soft excitation". That is the nitrogen is lifted exclusively to the metastable state. Other higher energy levels are not attained. This is quite dissimilar to all other prior art techniques for exciting nitrogen to its metastable state, including microwave discharge, condensed discharge, flame discharge, plasma discharge, high energy field discharge or the like.

Figure 2A:
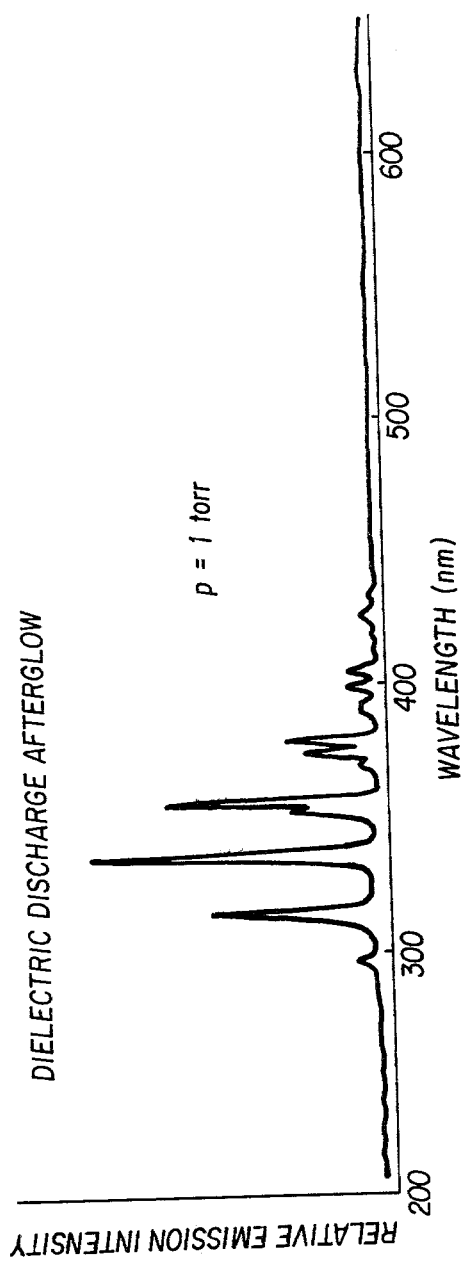
FIG. 2A shows the background emission from nitrogen gas excited by a dielectric discharge according to this invention.
Figure 2B:
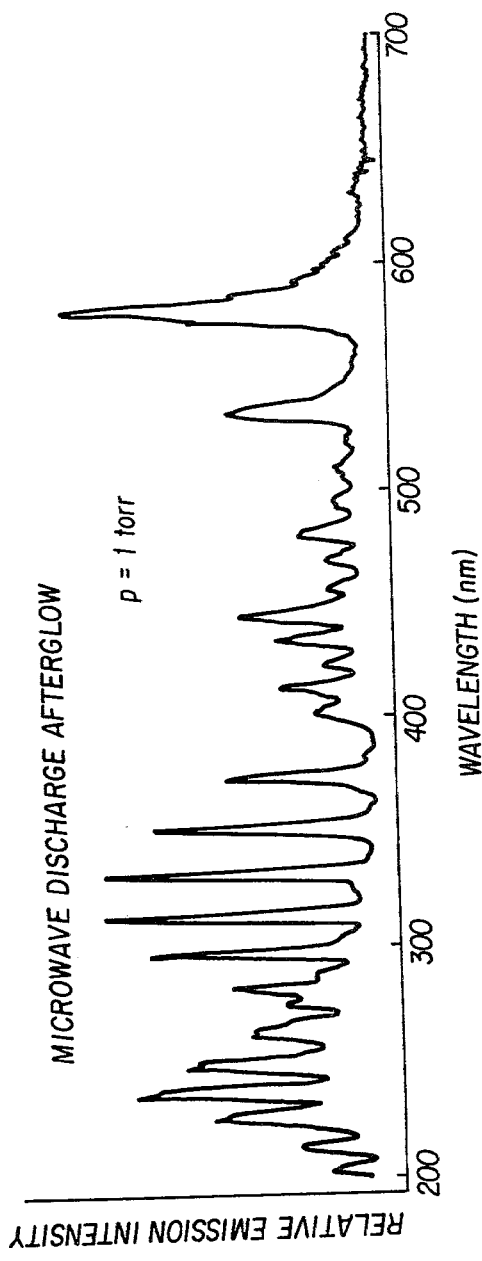
FIG. 2B shows the background emission from nitrogen gas excited by a microwave discharge.

As is known, nitrogen can be excited to many levels of excitation. In microwave discharge, for instance, the nitrogen is necessarily raised to levels much higher than the metastable state. The higher levels decay back down to lower levels with about 70% going down to the metastable state. The spectral result is a characteristic yellow afterglow emission which interfers significantly with the analysis (FIG. 2B). The present technique, in contrast does not produce levels of excitation higher than the metastable state, and therefore secondary, interfering emissions are eliminated (FIG. 2A).

Microwave discharge also breaks down the nitrogen molecules into their atoms which are then available for reaction with other gases such as oxygen. Thus, only a portion of the nitrogen atoms will be collisionally recombined so only a small portion will go down to the metastable energy state. Microwave generation therefore, produces only a small quantity of metastable nitrogen, but it also produces a large quantity of energy states and species and new compounds which provide an interference background spectra in which it is difficult to accurately distinguish the metastable nitrogen.

A significant difference between generating the metastable nitrogen according to the present invention as compared to the prior art, is that in the present invention the dielectric field imparts such a low level of energy to the nitrogen, that the nitrogen is kicked up directly to, and only to, the metastable state. In contrast, the prior art kicks the nitrogen up to higher excited state levels which then decay to the metastable state, or results in the production of substantial amounts of atoms, ions and new compounds. Very precisely, the use of the dielectric field enables the formation of the $A^3\Sigma_u{}^+$ state with no population of the higher vibrational levels of the $B^3\pi_g$ state. The nitrogen is not excited above the #6 vibration level above $B^3\pi_g$. Thus the metastable species generated here demonstrate only Begard-Kaplan emission with no 2nd positive emission, characteristic of $C^3\pi_g$ levels; no Herman-Kaplan emission, characteristic of H levels; no Goldstein-Kaplan emission, characteristic of C levels; and no 4th positive emission, characteristic of $D^3\Sigma_u{}^+$ levels. In short, levels of only 6.1–9.7 e.v. are attained.

Active nitrogen produced using the dielectric field will excite any atomic species having an excitable fluorescing electronic state about 6.1 e.v. or less above its ground state. It is estimated that about two-thirds of the elements of the periodic table will emit fluorescent radiation when excited by contact with active nitrogen; such emission has already been observed for 44 elements, including metals and many non-metals, such as chlorine. Mixtures of atoms can also be analyzed and even atoms in rather complex systems such as water in a helium stream can be analyzed. In fact, one of the significant advantages of the present invention is that a range of elements can be excited simultaneously with simultaneous analysis whereas prior art techniques required a high relative purity of the atom species being sampled to obtain good analytical results.

The nitrogen gas may be used alone as the exciting gas in the process of this invention, or it may be present together with another carrier gas. The partial presure of the nitrogen may be in the range of 1–300 torr, preferably 100–300 torr. Higher pressures of nitrogen tend to result in some quenching of the active molecules, whereas if the pressure is too low, the gas itself tends to act as a conductor with the tendency that spark discharges can occur producing ions and other species having energies above the preferred maximum.

One of the really interesting aspects of this invention is that the nitrogen gas used as the source gas need not be pure. In fact, quite surprisingly ordinary air can be used as the source gas. Although the oxygen does result in some background emission, insofar as one does not excite the nitrogen above the #6 vibrational level of the $B^3\pi_g$ state, the small background emission which does occur appears in the upper region of the spectrum, far from the region of analytical interest. In contrast, all prior art systems require very pure nitrogen source gas. The reason for this of course, is that oxygen will react with nitrogen atoms and ions which are formed whereas it has little effect on the metastable state species. Thus since the prior art processes generate considerably higher levels of excitation in which the metastable state is produced by decay, oxygen interference is a significant factor.

When nitrogen is admixed with other gases, such as argon, the total pressure of the gas can approach or reach atmospheric or above even though the partial pressure of the nitrogen is limited to 1–100 torr. In the present contemplation of the inventors, a lower pressure is used as the driving force to sweep the nitrogen through the dielectric field, into contact with the sample being analyzed and out of the system. Thus if the distance between the dielectric field and the sample-analysis chamber is reduced or eliminated, the pressure can approach atmospheric. Thus such simple expedients as an ordinary water aspirator can easily be used to draw the needed reduced pressure.

The present invention is so simple as compared to the prior art that one could simply carry a small bottle of pressurized argon-nitrogen which can be hooked up under field conditions to a small dielectric device and the system would be operational. This is particularly favorable when compared with prior art systems which require massive equipment, including water cooling apparatus, and high vacuum generating equipment.

Because there are such low proven requirements a field apparatus can be run off of an ordinary car battery, which, of course, would be impossible to do practically, with such prior art techniques for producing metastable nitrogen, such as microwave discharge.

The only limitation is that the nitrogen gas should be relatively free of quenching species, that is, of species which react with the metastable nitrogen molecules and deactivate them before they have had a chance to excite the sample species. Quenching species to be excluded include nitrogen single atoms, oxygen single atoms, sulfur dioxide, methanol, ammonia, nitric oxide and cyanogen. However, the presence of certain amounts of quenchers can be tolerated, and this is one of the advantages of the process of this invention.

Dielectric discharge is a very efficient method of producing activated metastable nitrogen molecules, and produces copious amounts of active nitrogen. Therefore the presence of quenchers in moderate amounts can be tolerated because enough active nitrogen molecules will be available to excite the sample species even in the presence of some quenching species.

The ability of the process of this invention to tolerate high pressures and relatively large amounts of quenching species represents a distinct advantage which is not possible by prior art techniques. Microwave discharges for instance, are limited to a maximum pressure of about 20 torr and can produce only a relatively low concentration of active nitrogen because, as discussed above, they produce quenching species simultaneously with the active nitrogen. Because of this low concentration of active nitrogen, the disclosed processes using a microwave discharge cannot tolerate the presence of quenching impurities in significant amounts. The method of this invention, on the other hand, which uses a dielectric discharge, is much moe tolerant of the presence of impurities and hence may use more economical, lower purity sources of nitrogen.

The large amounts of active nitrogen produced by the dielectric discharge also permit higher concentrations of the sample species to be analyzed. The linear dynamic range of methods using other types of excitation is limited by the relatively small amounts of active nitrogen produced by those methods. This problem is specifically discussed by Capelle, who notes that it is the factor which places the upper limit on the concentrations of sample species which can be accurately analyzed by his method. Using the process of this invention, concentration of sample species greater than $10^{18}$ atoms per cubic centimeter can be measured, which is some five orders of magnitude better than that obtained by the known process as disclosed by Capelle.

The dielectric discharge used in the process of this invention also produces an excited species having only a relatively weak background emission, that is, light emission in the absence of a sample. Microwave discharges and other discharges which produce species of higher energy and ions have a stronger background emission because these higher energy species either have a luminescence of their own or excite the nitrogen to higher energy levels which luminesce. The difference can be seen in FIGS. 2A and 2B which show the background emission from a nitrogen gas stream which has been excited by a dielectric discharge (FIG. 2A) and one which has been excited by a microwave discharge (FIG. 2B). It is evident that the background emission from the dielectric discharge contains fewer interfering lines than that from the microwave discharge. Thus the noise level in the detector will be lower for the process of this invention than for methods using other types of excitation and the minimum detectable concentration of sample species will, in general, also be lower.

Since the amount of active nitrogen present in the activating gas stream decreases steadily downstream from the dielectric discharge, one skilled in the art will recognize that if provision is made for rapidly mixing the sample with the active nitrogen stream and measuring the fluorescent emission soon after the stream leaves the generator, a higher concentration of quenching species can be tolerated in the active nitrogen stream. In extreme circumstances, the sample can even be incorporated into the same stream with the nitrogen and passed through the dielectric discharge so that the maximum amount of excited metastable nitrogen is present in association with the species to be analyzed. Such a procedure might be useful if it were necessary to operate the process with a high total pressure in the apparatus as in portable analytical instruments which might not have access to a source of vacuum.

Compounds containing elements analyzable by the process of this invention are often broken up by contact with the active nitrogen, and their component elements may accordingly be analyzed. Since the use of a dielectric discharge according to this invention produces copious amounts of active nitrogen, species can be analyzed even in fairly complex matrices wherein other quenching species may be present. Oxygen or the presence of water vapor will not interfere with the analysis, whereas it will interfere when the analysis is carried out by use of active nitrogen produced by the prior art techniques. For this reason the process according to his invention is expected to have wide applicability in analysis of clinical specimens such as blood and urine, in geological and soil analysis, in environmental and industrial process monitoring and in forensic sciences.

The dielectric discharge device used to produce the active nitrogen according to the process of this invention may be any conventional dielectric discharge device. The device shown schematically in FIG. 1 shows nitrogen gas passing between the electrodes from which it is isolated by a dielectric of high dielectric strength such as glass. For electrode gaps of a few millimeters and the usual gas pressures, the voltages used are typically between 1-16 kilovolts. Typically, the current through the device will be about 0.1-5 ma. Thus the total power dissipated in the discharge is about 10-100 watts, which is substantially less than that used in other methods of exciting metastable nitrogen atoms such as the microwave discharge which typically uses much more power. This has economic benefits, both in the lower consumption of power and in the fact that no special cooling system is required under ordinary conditions.

Glass is a preferred material for the dielectric because of its high dielectric strength and chemical inertness, although any dielectric having adequate dielectric strength and sufficient chemical inertness for a particular application may be used for such an application. The dielectric discharge may be produced by either direct current or alternating current. Alternating current is preferred however, because its use avoids charge accumulation effects with resulting fluctuations in current and voltage which may occur when direct current is used.

It will be theoretically possible to eliminate the dielectric glass and to merely pass a beam of low level electrons across a pair of electrodes. The problem with this expedient however, would be that if metal electrodes were used, the metal might sputter under the electron bombardment which would tend to interfere with the analysis. Neither carbon nor metal electrodes can be used practically since the activated nitrogen will be quenched to ground state by contact with the carbon or the metal surfaces.

Since the dielectric discharge device is relatively simple in construction, uses a simple low power and inexpensive source of energy for exciting the active nitrogen, requires relatively small amounts of gases in operation and can be operated at or near atmospheric pressures (for instance 0.5–1 atmosphere) it is readily adapted for use in small and portable instruments. This is in notable contrast to the other methods of producing active nitrogen especially those such as microwave discharges and inductively coupled plasmas which require complex and expensive equipment which is bulky, noisy, and uses a great deal of power, consume large amounts of gases, and often requires cooling water circulation systems to keep the power generator cool.

Having generally described the invention, a more complete understanding can be obtained by reference to certain specific examples which are provided herein for purposes of illustration only and are not intended to be limiting unless otherwise specified.

EXAMPLE

A dielectric discharge device was prepared from an ordinary laboratory condenser having two concentric glass tubes, the outer tube being sealed to the inner one and inlets being provided whereby a fluid can be passed through the annular space between the concentric tubes. The radial gap between the tubes was about 3 millimeters. An external electrode was provided by wrapping the outer tube with metal foil and an internal electrode was provided by filling the internal tube with a salt solution. The electrodes were connected to a high voltage transformer capable of providing an alternating current of about 5 milliamperes at about 8000 volts. Ultrahigh purity nitrogen gas was passed through a cold trap cooled to the temperature of liquid nitrogen in order to remove residual oxygen and then passed through the dielectric discharge device to generate a gas stream containing active nitrogen. The generation of the metastable state of nitrogen used herein is disclosed in Ung, Emission from the Afterglow of an Ozonizer Discharge through Nitrogen, Chemical Physics Letters, Vol 32, #1, pp. 193 and Noxon, Active Nitrogen at High Pressure, Journal of Chemical Phyics, Vol. 36, #4, pp. 926 (1962). The gas stream containing active nitrogen was then led into an analysis cell in which it was mixed with the material to be analyzed which was either supplied in gaseous form or vaporized and swept into the reaction chamber by a second stream of nitrogen. The contact between the sample species and the active nitrogen produced a flourescence characteristic of the sample species. The fluorescent emission was observed using a monochromator (Jarrel-Ash/Ebert f 3.5, 0.25 m) equipped with a 1P28 multiplier phototube operated by a conventional commercially available electrometer-high voltage supply. The intensity of the emission was recorded on a conventional strip chart recorder. Emission from the following elements has been quantified: mercury, zinc, tin and cadmium.

Figure 3:
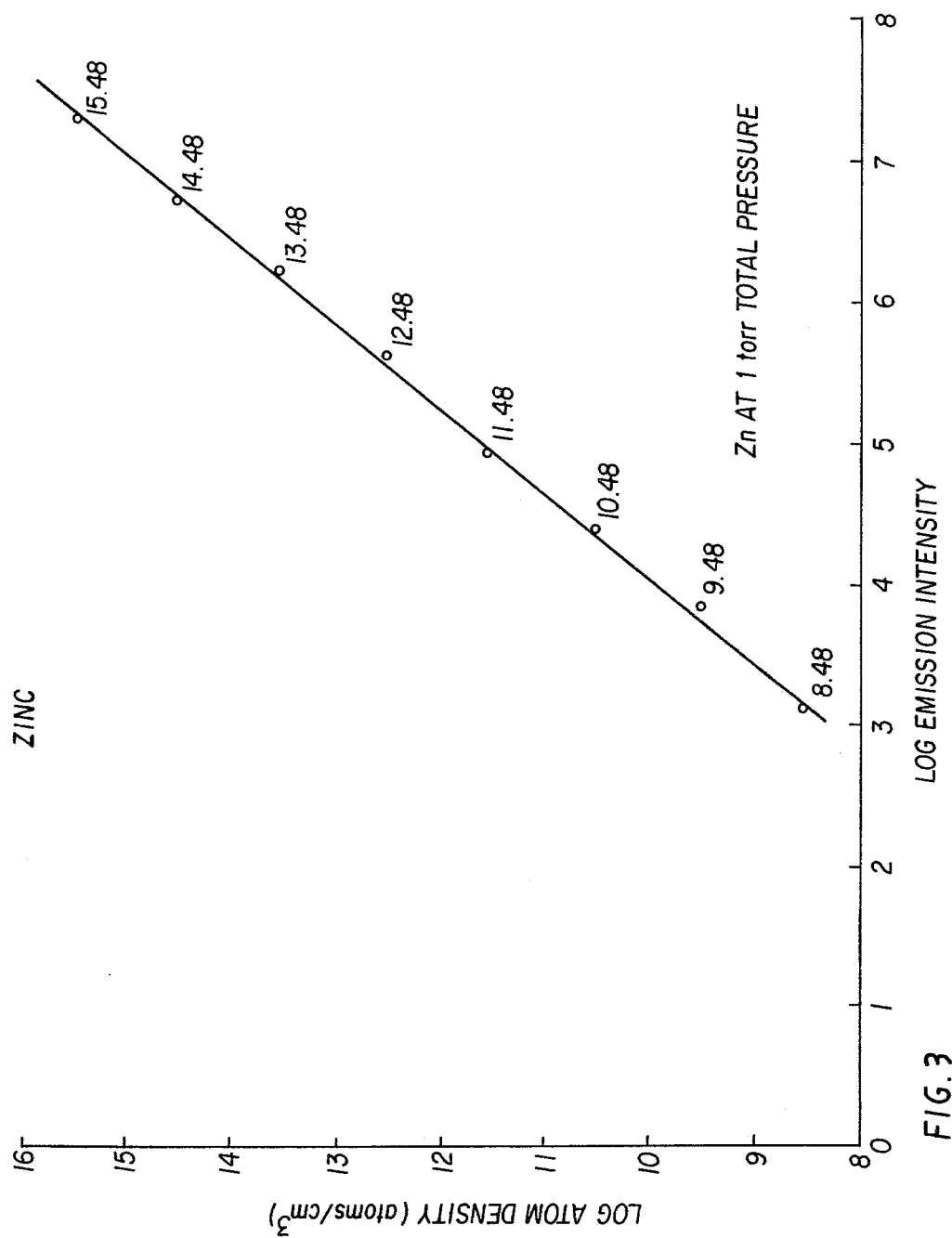

A portion of the calibration curve for zinc is shown in FIG. 3 where the emission intensity is shown to be a linear function of the concentration of zinc in the gas phase. In this case the nitrogen pressure in the dielectric discharge was 1 torr and the zinc was thermally atomized. Concentration or density was based upon using 5 $\mu l$ samples of $Zn(NO_3)_2$ solutions of different concentrations. Reproducibility was limited primarily by the reproducibility of the atomization source but was still better than ±10%. Lower concentrations could be measured with more sensitive detection apparatus. At higher concentrations there was no evidence of exhaustion of the active nitrogen, but the atomizer used in this case could not handle larger concentrations.

Figure 4:
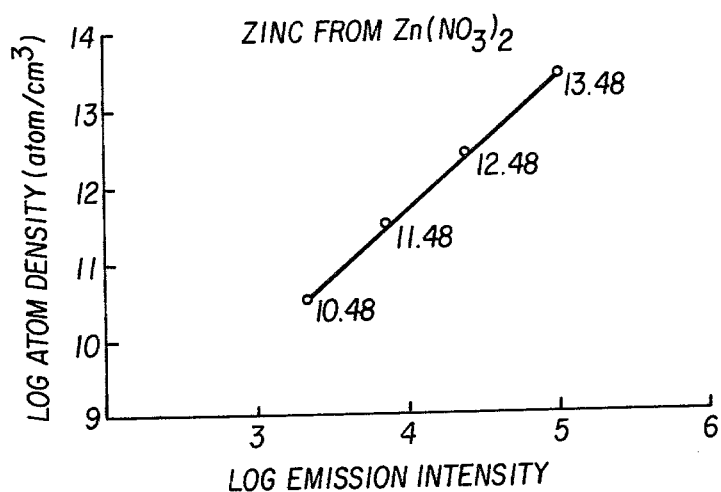

In FIG. 4 some of the same samples analyzed for FIG. 3 were thermally atomized but at a total pressure of 100 torr in the dielectric discharge apparatus (80 parts argon and 20 parts nitrogen). The good linear relationship and good reproducibility found at 1 torr is also evident at 100 torr.

Figure 6:
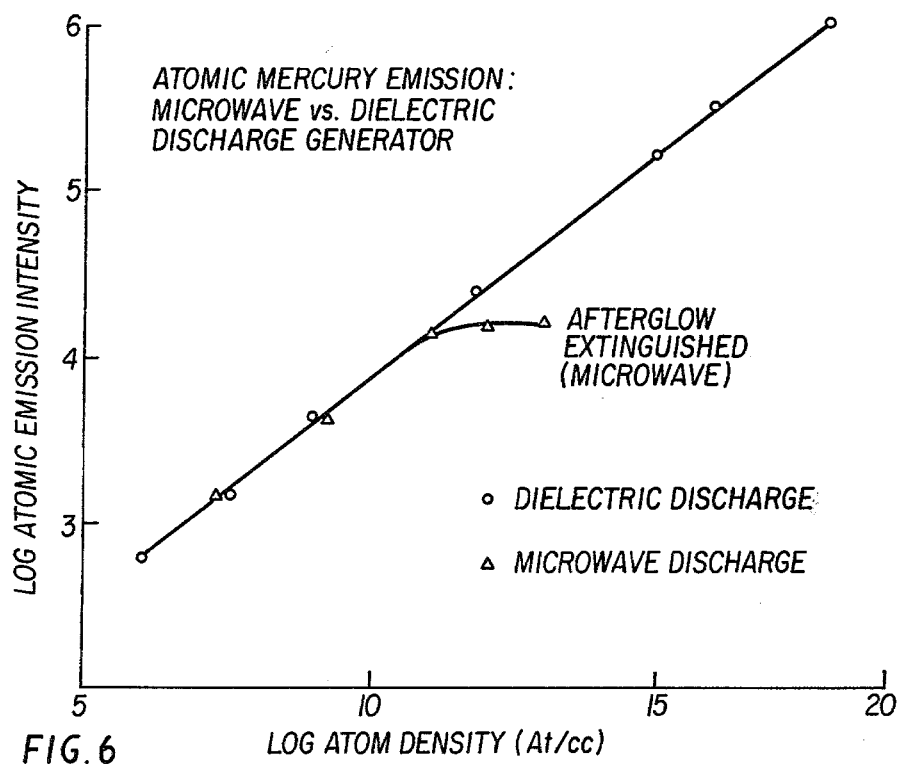
Figure 5:
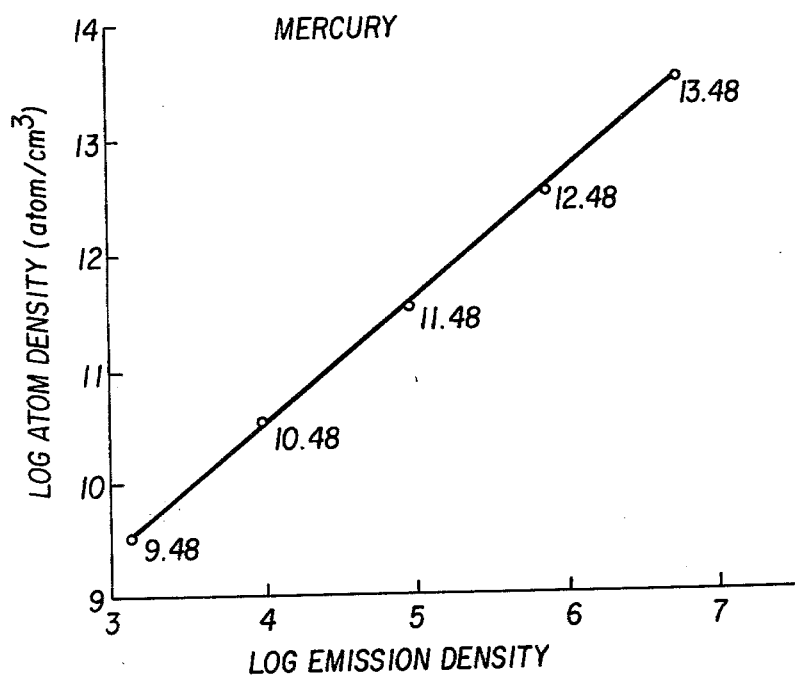

A portion of the calibration curve prepared using 5 $\mu l$ samples of $HgCl_2$, a thermal atomizer, and at a pressure of 1 torr in the dielectric discharge is shown in FIG. 5. A good linear relationship was obtained over a large dynamic range. In FIG. 6 a comparison is made between a microwave source of active nitrogen and the dielectric source described herein using the same reaction chamber. At lower concentrations the emission intensity depends upon the concentration of mercury atoms. However, as the concentrations of mercury increased, the active nitrogen from the microwave source was no longer in excess so the intensity no longer increased in a linear manner. Eventually at higher concentrations of mercury the microwave discharge afterglow was extinguished and no metal emission was observed. In the case of the dielectric discharge the linear relationship extended to very high concentrations of mercury.

Tin samples in the form of $SnCl_2$ (5 $\mu l$) at a pressure of 1 torr provided a similarly good straight-line relationship.

Cadmium samples in the form of $CdCl_2$ (5 $\mu l$) pressure 1 torr also gave an excellent straight-line relationship.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for analysis of atomic species which comprises directly forming metastable energy level molecular nitrogen by processing a stream of nitrogen containing gas through a dielectric field wherein said nitrogen is excited to a level of 6.1 to 9.7 e.v. and wherein essentially no excited species above the 6th vibrational level of the $B^3 \pi g$ energy state of molecular nitrogen is formed, and essentially no nitrogen atoms or ions are formed, admixing said excited nitrogen with a gas stream suspected of containing said atomic species to be analyzed whereby the energy level of said species is raised sufficiently to enable a fluorescent emmission as the energy level of said excited species decays to its lower energy state, detecting and analyzing the spectrum of said fluoresecent radiation to determine the identity and concentration of said element.

2. A process according to claim 1 wherein the partial pressure of nitrogen in said nitrogen containing gas is between 1 and 100 torr.

3. A process according to claim 1 wherein the partial pressure of nitrogen in said nitrogen containing gas is between 100–300 torr.

4. The method of claim 1 wherein said nitrogen-containing gas is air.

5. The method of claim 1 wherein water vapor is present in said gas stream suspected of containing said atomic species.

6. The method of claim 1 wherein said atomic species is characterized by having an excitable electronic state of about 6.1 e.v. or less above its ground state.

7. The method of claim 1 wherein a mixture of atomic species is simultaneously analyzed.

8. The method of claim 1 wherein the fluorescent radiation from said excited atomic species is detected upon a monochromator.

9. A process according to claim 1 wherein said nitrogen gas stream contains a carrier gas.

10. A process according to claim 9 wherein said carrier gas is argon.

11. The method of claim 9 wherein said nitrogen-containing gas has a pressure of near atmospheric.

12. An apparatus for analysis of atomic species which comprises dielectric excitation means for exciting molecular nitrogen in a nitrogen-containing gas to a higher energy metastable excited state, said dielectric excitation means including a flow channel having dielectric walls within which a stream of molecular nitrogen containing gas may be passed and further including opposing electrode means external to said flow channel and between which the flow channel is situated, said electrode means when connected to an electric power source being capable of establishing a dielectric field in said gas in said flow channel exciting molecular nitrogen to a metastable state, the excitation means in the apparatus producing nitrogen excited to a molecular metastable state while not exciting the nitrogen above the 6th vibrational level of the $B^3 \pi g$ energy state, said flow channel comprising two concentric dielectric tubes forming an annular space within and through which the nitrogen gas may be passed and wherein said opposing electrode means are an outer electrode means which is an electrode outside the outer tube and an internal electrode means defined by the internal tube, said apparatus also comprising means for introducing a stream of nitrogen containing gas into said flow channel and causing the nitrogen to pass through said excitation means, and means for admixing said gas subjected to the dielectric field with a gas stream suspected of containing the atomic species to be analyzed, and also comprising a reaction chamber wherein energy may be transferred from said excited nitrogen to said admixed atomic species whereby said atomic species if present is cause to emit fluorescent radiation and detecting means for detecting said fluorescent radiation.

13. The apparatus of claim 12 wherein said electrodes are capable of establishing a dielectric field which raises said nitrogen to a level of only 6.1–9.7 e.v.

14. The apparatus of claim 12 wherein the means for introducing nitrogen containing gas is a bottle of nitrogen and argon which can be fed to said excitation means.

15. The apparatus of claim 12 wherein the means for introducing nitrogen containing gas is air moving means, wherein air is brought into said excitation means.

16. The apparatus of claim 12 which contains means for controlling the partial pressure of the nitrogen containing gas in said system to a pressure of 1–300 torr.

17. The apparatus of claim 16 where said partial pressure controlling means is a water aspirator.

18. The apparatus of claim 12 where said detecting means is a monochromator.

19. The apparatus of claim 18 where said monochromator is connected to a recorder to record the wavelength and intensity of the emitted fluorescent radiation.

20. The apparatus of claim 18 wherein the dielectric of the dielectric tubes is glass.

* * * * *